US010660592B2

(12) United States Patent
König et al.

(10) Patent No.: US 10,660,592 B2
(45) Date of Patent: May 26, 2020

(54) METHOD FOR GENERATING A 3D DATA SET COMPLETE IN THE CENTRAL LAYER FOR VOLUME RECONSTRUCTION AND CONE-BEAM C-ARM X-RAY APPARATUS FOR PERFORMING THE METHOD

(71) Applicant: Ziehm Imaging GmbH, Nürnberg (DE)

(72) Inventors: Thomas König, Nürnberg (DE); Christof Fleischmann, Möhrendorf (DE); Eva-Maria Ilg, Nürnberg (DE); Lena Lochner, Nürnberg (DE)

(73) Assignee: Ziehm Imaging GmbH, Nürnberg (DE)

(*) Notice: Subject to any disclaimer, the term of this patent is extended or adjusted under 35 U.S.C. 154(b) by 203 days.

(21) Appl. No.: 15/981,772

(22) Filed: May 16, 2018

(65) Prior Publication Data

US 2018/0368791 A1 Dec. 27, 2018

(30) Foreign Application Priority Data

May 16, 2017 (DE) .................. 10 2017 004 705

(51) Int. Cl.
*A61B 6/00* (2006.01)
*A61B 6/10* (2006.01)
*A61B 6/03* (2006.01)

(52) U.S. Cl.
CPC .............. *A61B 6/4441* (2013.01); *A61B 6/03* (2013.01); *A61B 6/102* (2013.01); *A61B 6/4085* (2013.01);

(Continued)

(58) Field of Classification Search
CPC ..... A61B 6/032; A61B 6/4441; A61B 6/5205; A61B 6/037; A61B 6/4405; A61B 6/03; A61B 6/4085; A61B 6/102; A61B 6/467
See application file for complete search history.

(56) References Cited

U.S. PATENT DOCUMENTS

2014/0321612 A1 10/2014 Schäfer et al.
2015/0049856 A1* 2/2015 Ritschl ................ A61B 6/4078
378/14

(Continued)

FOREIGN PATENT DOCUMENTS

DE 10 2013 013 552 B3 7/2014

OTHER PUBLICATIONS

Examination Report for DE 10 2017 004 705.7 dated Jan. 25, 2018 in 68 pages.

(Continued)

*Primary Examiner* — David P Porta
*Assistant Examiner* — Fani P Boosalis
(74) *Attorney, Agent, or Firm* — Knobbe Martens Olson & Bear LLP

(57) ABSTRACT

This disclosure generally relates to a method and an apparatus for recording a 3D data set of an ROI (50) complete in the central layer by using a cone-beam C-arm X-ray apparatus (1) having a cone beam (32) with a cone angle (35) in the plane of the C-arm and having a virtual scan center (51) in the center of the ROI (50), wherein the scan is performed with a trajectory pair situated in the virtual scan center (51) and composed of a focus trajectory and a detector trajectory and wherein the rotational portion (402) of the detector trajectory is formed from piece-wise defined superellipses.

15 Claims, 5 Drawing Sheets

(52) U.S. Cl.
CPC .......... *A61B 6/5205* (2013.01); *A61B 6/4405* (2013.01); *A61B 6/467* (2013.01)

(56) References Cited

U.S. PATENT DOCUMENTS

| | | | |
|---|---|---|---|
| 2015/0305696 A1* | 10/2015 | Yamakawa | A61B 6/14 378/19 |
| 2016/0135775 A1* | 5/2016 | Mistretta | A61B 6/5247 600/411 |
| 2017/0067758 A1 | 3/2017 | Yaku | |
| 2018/0193669 A1* | 7/2018 | Jordan | A61B 6/4258 |

OTHER PUBLICATIONS

Examination Report for DE 10 2017 004 705.7 dated Apr. 13, 2018 in 26 pages.

* cited by examiner

METHOD FOR GENERATING A 3D DATA SET COMPLETE IN THE CENTRAL LAYER FOR VOLUME RECONSTRUCTION AND CONE-BEAM C-ARM X-RAY APPARATUS FOR PERFORMING THE METHOD

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present disclosure generally relates to mobile C-arm X-ray imaging systems and methods for generating images using the same.

Description of the Related Art

Mobile cone-beam C-arm X-ray apparatuses are increasingly being used in interventional X-ray diagnostics. Such a mobile cone-beam C-arm X-ray apparatus is movable on the floor and supports, on a chassis, a multiply adjustable holder in which a circular arc-shaped C-arm is movable along the periphery thereof in an orbital movement, wherein the C-arm supports at one end thereof an X-ray beam source and, at the other end thereof, an imaging X-ray beam detector, preferably a flat panel detector (FPD). All adjustment axes are preferably equipped with electrically controllable drives, so that by means of a movement controller, the X-ray recording unit consisting of an X-ray beam source and an X-ray beam detector can be positioned in space and/or moved along a focus trajectory and a detector trajectory to obtain a 3D data set. X-ray projection images are prepared after a positioning of the X-ray recording unit, or even during the movement on the trajectories. If the X-ray detector has a round entry window, as in, for example, an X-ray image amplifier or for a round FPD, then the beam field between the focal point of the X-ray tube is conical, and if a rectangular FPD is used, the beam field becomes pyramidal. In both cases, the term cone beam (CB) geometry is used in the literature. The beam is restricted by a primary beam diaphragm such that all the beams of the beam field are incident on the entry window of the X-ray beam detector. If an examination object is introduced into the beam field, then an X-ray projection of the spatial region of the examination object present within the beam field can be recorded. A motor-adjustable diaphragm system is preferably arranged between the focal point and the examination object in order to restrict the beam field to a measurement field (region of interest, ROI). All the processes of the image recording are controlled by an image-recording controller that is synchronized with the movement controller. The recorded X-ray projection images are processed together with data from the movement controller and the image-recording controller in an image-processing computer.

In interventional X-ray diagnostics, the region around the patient table is occupied by a number of devices, and in addition, a working region for the persons who carry out the intervention or assist with the intervention must be guaranteed. A mobile cone-beam C-arm X-ray apparatus used for interventional diagnostics is moved with predetermined basic positions of the adjustment axes, preferably approximately perpendicular to the longitudinal axis of the patient table, up to the examination object such that the preferably vertically arranged C-arm plane contains a virtual scan center in the interior of the ROI and this vertical scan center lies on the vertically oriented central beam of the X-ray recording unit. In this working position, the wheels of the chassis are blocked and the X-ray recording unit of the cone-beam C-arm X-ray apparatus is brought into the desired position and orientation by means of multiple, preferably motor-controlled adjustment axes. The motor-controlled adjustment axes can be controlled automatically by means of a movement controller of a central computer unit in the X-ray system or manually by means of suitable input means. If scans for recording an image series of projection images are prepared during the intervention, it is desirable that the movement of the X-ray recording unit and the central beam remain in an originally adjusted plane. Any movement component perpendicular to the original C-arm plane would increase the space requirement of the cone-beam C-arm X-ray apparatus in the direction of the longitudinal axis of the patient table and produce an increased risk of collision with other apparatus or/and would restrict the working space for the persons involved in the intervention. It is particularly advantageous for handling the cone-beam C-arm X-ray apparatus if the C-arm plane is vertical in the room. Then only a narrow corridor need be kept free as movement space for the x-ray recording unit during a scan. If the mobile cone-beam C-arm X-ray apparatus is not being used for a short time, it can be moved along the floor on wheels on the chassis away from the patient table perpendicular to the longitudinal axis of the patient table into a parking position and quickly moved from there back into the working position.

The image data from a series of 2D X-ray projections of the ROI that were recorded with different X-ray projection geometries are required for the reconstruction of the 3D X-ray volume of an ROI. In the process, the X-ray beam source and the imaging X-ray beam detector such as a flat-panel detector FPD are moved around the ROI, and X-ray projection recordings of the examination object are made during the movement.

With a mobile cone-beam C-arm X-ray apparatus, it is preferred to record so-called short scans, in which the angle of rotation range is less than 360°. If the cone-beam C-arm X-ray apparatus has an isocentric C-arm, in which the central beam runs through the circular center of the C-arm arc, a planar rotation scan can be recorded by rotating the C-arm about the center point thereof, the angle of rotation range depending on the arm length and the radius of the C-arm.

If the cone-beam C-arm X-ray apparatus has a non-isocentric C-arm, in which the circular center of the C-arm arc is outside the circular segment formed by the central beam and the C-arm profile, then a rotational scan can be recorded with such a non-isocentric cone-beam C-arm x-ray apparatus as with an isocentric C-arm, if the X-ray recording unit is guided on the C-arm about a virtual isocenter in such a manner that the holder of the C-arm is adjusted in the C-arm plane for each position so that the central beam runs through the virtual scan center. The C-arm holder can be adjusted in such a manner that the distance of the entry window of the X-ray beam detector from the virtual scan center is the same for each projection geometry. It is also possible, however, to take scans with a variable distance between the entry window of the x-ray beam detector and the virtual scan center, with an identical distance between the x-ray emitter and the x-ray beam receiver.

In order to be able to determine a 3D model of the X-ray absorption of the voxels of a disc-shaped ROI having a thickness of one voxel from a set of x-ray projections by using an analytical computation process, it is necessary to have a complete projection data set. In this data set, the integrals of the X-ray absorption values for all projection lines in an angle range of 0° to 180° are present for each voxel of the ROI.

A complete projection data set is obtained for a disc-shaped ROI in the C-arm plane if the ROI is completely captured by a cone beam and the x-ray recording unit associated with the cone beam is rotated about the center point of the ROI with a rotational angle range of 180° minus the cone angle, and the missing angles necessary for completeness of the 3D data set in an angle range that corresponds to the cone angle are obtained by translational movement of the X-ray recording unit. If the rotational movement of the X-ray receiving unit is a circular arc, then the term "arc-shift trajectory" is in common use for the planar trajectories of the X-ray beam detector and the X-ray beam emitter composed of rotational and translational portions.

For the rotational movement of the X-ray recording unit about a virtual scan center and for the translational movement relative to the virtual scan center, a cone-beam C-arm X-ray apparatus is used in which the holder of the C-arm, wherein the arm is mounted movably along the periphery of the arm, is correlated in the C-plane by means of two preferably orthogonal adjustment axes with the movement of the C-arm in the orbital adjustment axis. Such a cone-beam C-arm X-ray apparatus is known from German Patent No. DE10153787B4 by the applicant. The orbital movement of the C-arm therein is correlated with the adjustment of the holder for the C-arm in the horizontal and vertical directions in the C-plane in such a manner that defined conditions for the projection geometry are maintained.

In order to perform a scan for solving the stated imaging problem with a virtual scan center using a multiply adjustable C-arm x-ray apparatus, the patient is positioned on a preferably adjustable patient table and fixed thereto in such a manner that the patient cannot change position during recording of the projection images. The controllers of known x-ray apparatuses have so-called organ programs, in which the ROI is selected in an anatomy model and input into the controller of the X-ray apparatus via an input device. In addition to the position of the organ to be examined, the selection also relates to the size and/or thickness of the patient to be examined. Patient envelope curves are stored in the memory of the movement controller, from which an envelope curve around the table and the patient body is selected, which defines a spatial region in which no moving parts of the cone-beam C-arm X-ray apparatus may enter for a selected scan plane. If there is nevertheless a threat of contact of a part of the cone-beam C-arm X-ray apparatus with the patient or parts of the table during the scan, a collision warning system is provided which stops the movement of the cone-beam C-arm X-ray apparatus if there is a threat of a collision.

By selecting the organ to be examined from the organ program of the cone-beam C-arm X-ray apparatus, the virtual scan center is selected in an anatomy model. For example, if a spinal column examination is selected, the distance between the surface of the patient table and the virtual isocenter is considered to be especially large and the location of the virtual isocenter is assumed to be in the center plane of the patient table. To achieve collision-free trajectories in this case, it is especially important to take into consideration the lower parts of the patient table.

On the other hand if a shoulder examination is selected in the organ program for example, the virtual isocenter is a slight distance above the upper edge of the patient table and in the vicinity of the lateral boundary of the patient table. To achieve collision-free trajectories in that case, it is important to give particular consideration to the lateral table edges and the patient envelope curve, especially for heavy set patients.

Selecting the organ program defines the position of a point of interest (POI) in which the virtual scan center is to be placed for the stated imaging task with respect to the patient cross-section and in relation to the tabletop of the patient table.

Before the examination begins, the cone-beam C-arm X-ray apparatus is moved up to the patient by means of the rollers on the floor, in a defined base position, preferably with the C-arm surface perpendicular to the patient longitudinal axis, in such a manner that the central beam of the C-arm, preferably marked by a light pointer, runs in the vertical and horizontal orientation through the center of the ROI. The coordinate systems of the cone-beam C-arm X-ray apparatus and of the patient are referenced relative to one another by such a positioning of the cone-beam C-arm X-ray apparatus in relation to the patient and the patient table. Performing the referencing between the cone-beam C-arm X-ray apparatus and the patient table with an increased accuracy by using a position detection system or by measurements with a calibration phantom is a known measure.

In a known non-isocentric cone-beam C-arm X-ray apparatus, the holder of the C-arm is tracked in the C-plane with two linear movement axes in such a manner that a virtual isocenter is generated, for example. The size of the cross-section that can be circumnavigated without collisions is limited by the focus-detector distance and by the maximum displacement paths of the linear movement axes. Particularly if a scan is to be recorded with a rotational and with translational trajectory portions ("arc shift"), it has been found that sufficiently long adjustment paths in the linear movement axes for complete passage of the translational trajectory portions may not be available if there are large distances between the selected virtual scan center and the fixedly prescribed mechanical center of rotation, namely the center of the C-arm circular arc, as is necessary to avoid collisions with obese patients. In this case, an incomplete 3D data set of the central layer would be present after the end of the scan, which leads to undesired quality defects in the reconstructed 3D volume.

If there were a threat of a collision of parts of the C-arm with the patient and/or the patient table during a scan, the scan would be stopped. In the best case, the scan could be continued after a manual correction of the position of the C-arm with a different trajectory stored in the memory of the movement controller. In the least favorable case, the scan would have to be restarted with a new trajectory. In all cases, however, the recording of the scan for solving a prescribed imaging problem would take unnecessary extra time and/or lead to a poorer reconstruction quality and/or to an increased radiation exposure for the patient. Even recognized collision risks in a scan without radiation for the purpose of checking the danger of collision lead to a longer time overall for solving the imaging problem.

There is a need for a method for faster definition and recording of scans with a C-arm having a limited orbital adjustment range of less than 180°, which generates a 3D data set that is complete or nearly complete in the central layer, without, during the scan, a collision of parts of the x-ray recording unit with the patient, parts of the patient table or instruments in the surroundings of the patient, which would lead to a cancellation of the respective scan.

A complete projection data set for a disk-shaped ROI in the central layer that was recorded with a conical beam geometry can also be used in an approximation method outside the central layer by means of a Feldkamp algorithm for reconstruction.

If a disc-shaped X-ray volume is reconstructed from an incomplete projection data set, then artifacts appear in the reconstituted X-ray volume that can considerably interfere with a diagnosis of the conditions in the ROI. It is therefore desirable to minimize the artifacts in the ROI by recording a complete projection data set.

An X-ray system is known from DE3604955A1, in which a patient envelope curve is defined for a patient to be examined on a patient table, wherein the movement controller of the X-ray apparatus shifts the movable components in such a manner that they do not penetrate into the interior of the patient envelope curve.

DE102013013552B3 discloses a method for producing a 3D data set that is complete in the central layer by means of a C-arm having an orbital rotation range of less than 180°, in which the trajectories of the x-ray emitter and the x-ray detector lying in a single plane consist of a circular rotational movement and an adjoining translation. If there is a risk of a collision of the emitter or the X-ray detector with the patient or with parts of the patient table, the X-ray recording unit is displaced linearly along the central beam in order to avoid a collision during further passage through the trajectories.

An x-ray CT scanner and a scanning method are known from DE102006033882A1, in which a trajectory without a shift component is provided and in which the rotational part of the trajectory has a variation of the enlargement or resolution.

A method for generating an image sequence for a 3D reconstruction is known from DE102007044368A1, in which a rotational trajectory without a shift component is calculated after inputting a collision volume and an ROI with variation of the enlargement scale.

A method and an apparatus for recording X-ray images for three-dimensional image reconstruction are known from DE102009031165A1, in which a trajectory is composed of arc and line segments, wherein the ROI is always contained completely in the beam cone.

A method and a device for rotational sensing of an object using a C-arm system are known from DE102011086754A1, in which the trajectories are generated by superimposing two circular movements.

A method for sensing an object by using a fan-shaped beam is known from DE4016245C2, in which a trajectory composed of a circular arc and a line is proposed.

A method and an apparatus for carrying out a cone beam computer tomography (CB-CT) are known from WO15073048A1, which provides that the scan diameter of a volume to be scanned is enlarged by a trajectory having rotational and translational components.

A method for generating complete trajectories with a rotating X-ray imaging system is known from EP2068713B1, in which the translational components of the trajectory are produced by shifting the object.

A method for reconstruction of a three-dimensional image volume is known from DE102006041033A1, wherein a trajectory with a shift component is provided and wherein a cone-beam C-arm X-ray apparatus based on a robot or a cone-beam C-arm X-ray apparatus with an adjustable X-ray emitter and an adjustable detector is provided to carry out the method.

The use of superellipses and hyperellipses for describing boundaries of a face in order to extract biometric data of a face and for recognition of the face and for positioning of the head of a patient for a dental x-ray apparatus is known from document EP2130491B1.

A rotational scan trajectory about a scan center is known from DE102007044368B4, in which the detector input window contacts an elliptical envelope curve of an object tangentially.

A method for describing curved planar paths with superellipses by using parametric data is known from DE2254913A.

A method for modeling vascular trees by using superellipses is known from document DE102008007231A1.

In the methods known from the prior art for recording a complete set of X-ray projections for the analytical reconstruction of a disc-shaped X-ray volume lying in the plane of the C-arm by using a cone-beam C-arm X-ray apparatus having an orbital angle adjustment range of 180° or less, in which the holder of the C-arm can be adjusted in the C-plane in two independent spatial directions by means of linear adjustment units having limited adjustment paths, there is the difficulty with obese patients and with a POI to the side of the longitudinal body axis of the patient, of determining a trajectory pair for an imaging task composed of a detector trajectory and a focus trajectory for the X-ray recording unit that can be traversed without the risk of a collision of parts of the cone-beam C-arm X-ray apparatus with the patient, parts of the patient table or with device parts arranged on the patient such as sensors, retaining devices, instruments or the like.

There is a need for a method for determining a trajectory pair for collision-free recording of a complete projection data set.

SUMMARY OF THE INVENTION

A problem addressed by the invention is, for a predetermined imaging task on a patient, that of creating a method for faster definition and recording of a series of X-ray projection recordings in a scan with a cone-beam C-arm X-ray apparatus having a limited orbital adjustment range of less than 180 degrees and limited horizontal and vertical adjustment ranges in the C-plane, which have trajectories for scans relative to a virtual scan center for a point in the center of the entry window of the X-ray detector and for the focus of the X-ray tubes, which trajectories contain rotational and translational portions and generate a 3D data set that is complete in the central layer, without having to expect that there may be a collision between parts of the cone-beam C-arm x-ray apparatus and the patient, parts of the patient table, more particularly the patient table top, or instruments in the vicinity of the patient that would result in an unforeseen poorer quality of the 3D reconstructions in the event of interruption of the current scan or an unplanned higher radiation exposure of the patient or/and a longer examination time due to possible repetition of a scan with modified trajectories for emitter and detector.

A problem addressed by the invention can be solved by a method wherein a cone-beam C-arm X-ray apparatus described herein is used to carry out the method.

The inventors recognized that the collision-free volume formed by the movement of the C-arm can be enlarged and advantageously adjusted in shape to the requirements of the position of the virtual scan center and the dimensions of the patient and/or the patient table if superelllipses are used for the rotational portion of the focus or detector trajectory at least in certain portions.

The solution to the problem can comprise calculating a bundle of trajectories with rotational portions in the form of piecewise defined superellipses and storing it in the memory of the cone-beam C-arm X-ray apparatus, and after selecting an organ program for the imaging task, selecting a trajectory pair composed of a focus trajectory and a detector trajectory considered suitable for this task, and after orienting the cone-beam C-arm X-ray apparatus with the motorized horizontal and vertical adjustment axes of the C-arm holder in predefined basic positions relative to the POI and the section plane in a patient on a tabletop of a patient table, carrying out a scan with the selected trajectory pair, and recording X-ray projections at predetermined points.

The method according to an embodiment of the invention for recording a scan comprising a series of 2D x-ray projections from a cone-beam C-arm X-ray apparatus that allows an analytical 3D volume reconstruction of a disk-shaped ROI of the central layer utilizes a planar focus trajectory comprising at least three continuous portions, on which trajectory the focus of the X-ray beam source is traversed while recording X-ray projection images, wherein the X-ray beam source emits a cone beam in the direction of an imaging X-ray detector, more particularly a flat-panel detector FPD. The cone beam is formed in the plane of the focus trajectory that contains the ROI with the virtual scan center as a cone beam having a cone angle, wherein the central beam of the cone beam is on the angle bisector of the cone angle and perpendicular to the beam entry window. Such a cone beam geometry is used as the basis for a 3D reconstruction from 2D projection recordings. Mechanical insufficiencies of the C-arm mechanism have the effect that the central beam does not run precisely through the virtual scan center during rotational portions of the trajectories. The mechanical deviations from the ideal geometry are determined and corrected by single or repeated calibration measurements.

It is provided within the scope of one embodiment of the invention to also use the complete projection data set for a disc-shaped ROI in the central layer that was recorded with a cone beam geometry for approximation outside the central layer, for example by a Feldkamp algorithm for reconstruction. Before the beginning of the scan, the C-arm plane is set up in space and the C-arm in the orbital movement axis is positioned in a first extreme position, in which the holder is engaged at one end of the C-arm with the X-ray beam source and the adjustable holder of the C-arm is positioned such that the ROI is outside the circular segment formed by the C-arm and the central beam, and a first limiting beam of the cone beam originating from the focal point on the side of the central beam facing away from the C-arm is tangential to the ROI. The plane of the C-arm remains spatially fixed during the recording of the scan.

In the first of the three portions of the focus trajectory, the C-arm remains positioned in the first extreme position of the orbital movement axis and the holder of the C-arm is displaced collision-free in parallel in the plane of the C-arm until the central beam runs through the virtual scan center and the ROI lies completely inside the cone beam.

In the second portion of the focus trajectory, which adjoins the first portion, the C-arm is moved along the orbital movement axis by an angle of 180° minus the cone angle from the first extreme position into the second extreme position, in which the holder is engaged at the other end of the C-arm with the X-ray beam detector wherein the holder, in the case of a non-isocentric C-arm or in the case of an isocentric C-arm with an ROI not present in the isocenter in the plane of the C-arm, is moved parallel in such a way that the central beam runs approximately through the virtual scan center for each position of the orbital movement axis and the ROI is completely inside the cone beam.

A rotational trajectory of a point on the input window of the flat-panel X-ray detector FPD is linked to the rotational focus trajectory. A rotational focus trajectory is likewise linked to a rotational detector trajectory. The curves provided for the rotational trajectory of an arbitrary reference point on the C-arm are parameterized superellipses, which can vary piecewise or continuously in width and height and in their rotational position relative to the horizontal line running through the virtual scan center.

In the third portion, which adjoins the second portion of the focus trajectory, the C-arm remains positioned in the second extreme position of the orbital movement axis and the holder is displaced in parallel, collision-free in the plane of the C-arm until a second limiting beam on the side of the central beam facing the C-arm is tangential to the ROI.

The focus of the X-ray beam source can be traversed on the focus trajectory between a starting point and an endpoint as well as a reference point on the input window of the FPD in an arbitrary direction on a trajectory between a starting point and an ending point. In the process, each point of a detector trajectory arises from a point of the associated focus trajectory and vice versa, because the focus is mechanically rigidly linked to the FPD by the C-arm and because conditions for the position of the central beam with respect to the virtual scan center during the scan are specified.

DETAILED DESCRIPTION OF THE PREFERRED EMBODIMENT

Figure 1A:
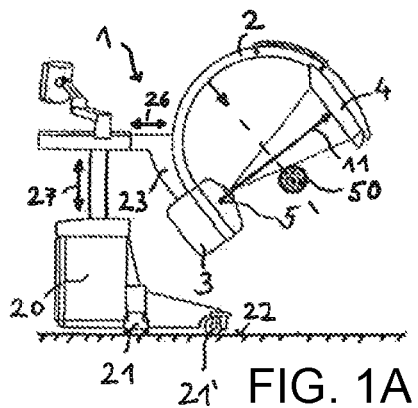
FIGS. 1A-1D illustrate a cone beam C-arm X-ray apparatus with limited rotational range.

Certain embodiments of the invention will be explained with reference to figures.

FIGS. 1A-1D present a cone-beam C-arm X-ray apparatus 1 having a limited rotational range in four different phases of the recording process for recording a complete projection data set for an ROI 50. The cone-beam C-arm X-ray apparatus 1 shown for the sake of example in FIG. 1A has an apparatus cart 20 that is movable along the floor 22 by means of wheels 21, 21'. Mounting the C-arm 2 adjustably on a stationary floor or ceiling support is also provided within the scope of certain embodiments of the invention, however.

The C-arm of FIGS. 1A-1D is a non-isocentric C-arm, in which the circular center point of the C, namely the mechanical center of rotation of the C-arm in its holder, is not on the central beam vector 11, 12, 13, 14. In order to be able to record a rotational scan of an examination object having a measurement field (region of interest, ROI), the holder 23 of the C-arm 2 must be adjusted during the scan in correlation with the orbital movement in the orbital movement axis 25 in the plane of the C-arm 2 in such a manner that the central beam vector 11, 12, 13, 14 always runs through the virtual scan center 51.

The volume to be reconstructed preferably has the shape of a cylinder having a height H, the cylinder axis being perpendicular on the plane of the C-arm 2. In the plane of the C-arm 2, the section through the cylindrical volume to be reconstructed preferably constitutes a circular ROI 50, and the penetration point of the cylinder axis through the plane of the C-arm 2 constitutes the virtual scan center 51 located in the circular center of the ROI 50. The plane of the C-arm 2 remains stationary during the recording of the X-ray projections. It is particularly advantageous for the space requirement of a cone-beam C-arm X-ray apparatus 1 during the recording of a scan if the plane of the C-arm is vertical in the room. It is also provided within the scope of certain embodiments of the invention to perform the scan with a different position of the spatially fixed plane of the C-arm 2. This is of particular interest if a section plane of the examination object that is not vertical in the room is to be reconstructed artifact-free and the examination object cannot be oriented such that the desired section plane with the ROI 50 contained therein is vertical in the room.

Figures 1B, 1C:
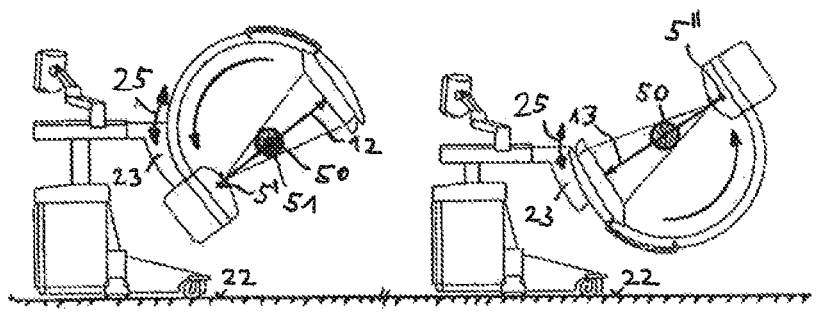
Figure 1D:
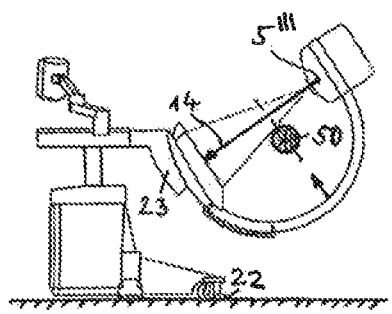

FIGS. 1B and 1C show the end positions of a rotational scan with a non-isocentric C-arm 2. The trajectories of the focus 5', 5" and the tip of the central beam vector 12, 13, which constitutes the center point of the beam entry window of the X-ray beam detector 4, are on two spatially fixed trajectories with the stationary virtual scan center on the central beam.

The mobile cone-beam C-arm X-ray apparatus 1 shown in FIG. 1A has an apparatus cart 20 which supports a multiply adjustable C-arm 2 that bears at one end an X-ray beam source 3 having a focus 5, and at the opposite end of the C-arm 2, an X-ray beam detector 4. Between the focus 5 and the center point of the X-ray beam detector 4, a central beam vector 11 is shown, which lies in the plane spanned by the C-arm 2. The C-arm 2 is supported movably along the periphery thereof in a holder 23. This so-called orbital movement axis 25 is marked by a double arrow in FIG. 1B. The holder 23 is movable relative to the floor 22 or the device cover 20 in the plane spanned by the C-arm 2. In the example of FIG. 1A, the holder 23 is movable with a horizontal movement axis 26 and a vertical movement axis 27. In a predetermined angular position of the central beam vector 11 relative to the floor 22, the C-arm is displaceable in parallel in the movement range of the horizontal movement axis 26 and the vertical movement axis 27 in the plane of the C-arm 2, while maintaining its direction.

The cone-beam C-arm X-ray apparatus 1 is intended to provide a projection data set for an ROI having a virtual scan center 51, the data set being complete with regard to a Feldkamp 3D reconstruction of a disc-shaped ROI, for example. The C-arm 2 shown for the sake of example in FIGS. 1A-1D is a non-isocentric C-arm, in which the central beam vector 10, 11, 12, 13 does not run through the arc center, not shown, of the C-arm. During a displacement of the C-arm 2 in the holder 23 along the periphery of the C-arm 2, the central beam vectors 10, 11, 12, 13 do not run through a spatially fixed point, but rather are each tangent to a circle around the virtual scan center 51. An isocentric C-arm is simulated by a synchronous guidance of the C-arm 2 in the horizontal movement axis 26 and the vertical movement axis 27 during the orbital movement in the orbital movement axis 25.

Figure 3:
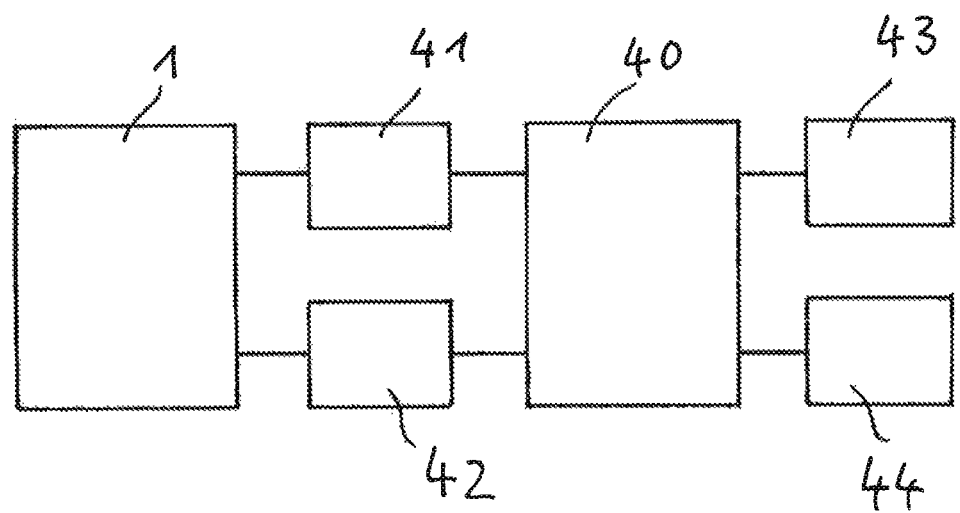
FIG. 3 illustrates controller architecture of a cone-beam C-arm X-ray apparatus.

The movement in the horizontal movement axis 26, the vertical movement axis 27 and the orbital movement axis 25 is accomplished by motor power, the movements being controlled in a movement controller 41 in FIG. 3.

The C-arm 2 in FIGS. 1A-1D has a limited rotational range of less than 180° in the orbital movement axis 25. With a rotational range limited in such a manner, it is not possible to record a complete projection data set for an analytic reconstruction of the disc-shaped cylindrical x-ray volume using the Feldkamp method. In order to generate the complete data set for the disk-shaped ROI 50 of the central layer with a thickness of one voxel in the plane of the C-arm 2, the missing projection data must be recorded with additional planar trajectories. For this purpose, the C-arm 2 in FIG. 1A is first positioned in a first extreme rotational position, in which the holder 23 at one end of the C-arm 2 engages with the x-ray beam source 3 in such a manner that the cone beam running between the focus 5, 5, 5", 5'" and the X-ray beam detector 4 just barely does not pass through the region of interest 50 and a first limiting beam of the cone beam 32 lying on the side of the central beam vector 11, 12, 13, 14 facing away from the C-arm 2 is tangent to the ROI 50.

Originating from this starting position, the C-arm 2 is moved, with the direction of the central beam vector 11 in the first extreme rotational position of the C-arm 2 remaining constant, in the direction of the virtual scan center 51 by movements in the horizontal movement axis 26 and the vertical movement axis 27, until the central beam 12 runs through the virtual scan center 51 in the center of the ROI 50 in the position of the C-arm 2 as shown in FIG. 1B. In the position of the C-arm 2 in FIG. 1B, the entire ROI 50 is completely within the beam cone of the cone-beam C-arm X-ray apparatus 1.

Between the position of the C-arm 2 in FIG. 1B and the position of the C-arm 2 in FIG. 1C, the central beam vector 12, 13 rotates such that it always passes through the virtual scan center 51 and is moved from the first extreme rotational position in FIG. 1B into the second extreme rotational position in FIG. 1C, in which the holder 23 engages X-ray beam detector 4 at the other end of the C-arm 2. The two extreme rotational positions of FIGS. 1B and 1C characterize the end positions of the movement of the C-arm 2 in the holder 23 along the orbital movement axis 25. The two extreme rotational positions are apart from one another by an angle of at least 180° minus the cone angle on the orbital movement axis.

Proceeding from the position of the C-arm 2 in FIG. 1C, the C-arm 2 is moved away from the ROI 50 with an unchanged direction of the central beam 13 in the second extreme rotational position of the C-arm 2 by movements in the horizontal movement axis 26 and the vertical movement axis 27 until the ROI 50 is just barely completely outside the cone beam and a second limiting beam of the bean cone 32 is tangent to the ROI 50 on the side of the central beam vector 11, 12, 13, 14 facing the C-arm 2.

For an isocentric C-arm, the rotation of the central beam vector 12, 13 between the positions of the C-arm 2 in FIGS.

1B and 1C can be accomplished solely by the orbital movement along the periphery thereof in the holder 23, whereas a tracking by the horizontal movement axis 26 and the vertical movement axis 27 during the orbital movement in the orbital movement axis 25 is necessary in a non-isocentric C-arm as in FIGS. 1B and 1C. For an isocentric C-arm, it can be advantageous not to place the virtual scan center in the isocenter of the C-arm but rather close to the detector between the isocenter and the FPD for example. In this case it is also necessary for an isocentric C-arm to displace the holder of the C-arm in the plane of the C-arm in order to keep the central beam on the virtual scan center.

In the practical application of the method according to the description of FIGS. 1A to 1C, the C-arm is first brought collision-free into the position at the beginning of the scan as illustrated in FIG. 1A. This positioning movement is done without the emission of radiation and the projection recordings of the scan are first recorded after starting the scan movement. At the conclusion of the scan, the C-arm 2 is in the position illustrated in FIG. 1D.

The direction in which the trajectories of the X-ray beam source and the detector are traversed is irrelevant for the method for recording the projection data set. It therefore makes no difference if the C-arm 2 is in the position shown in FIG. 1D at the beginning of the scan. At the conclusion of the scan traversed in the reverse direction compared to the description of FIGS. 1A to 1D, the C-arm 2 is in the position shown in FIG. 1A.

Figure 2:
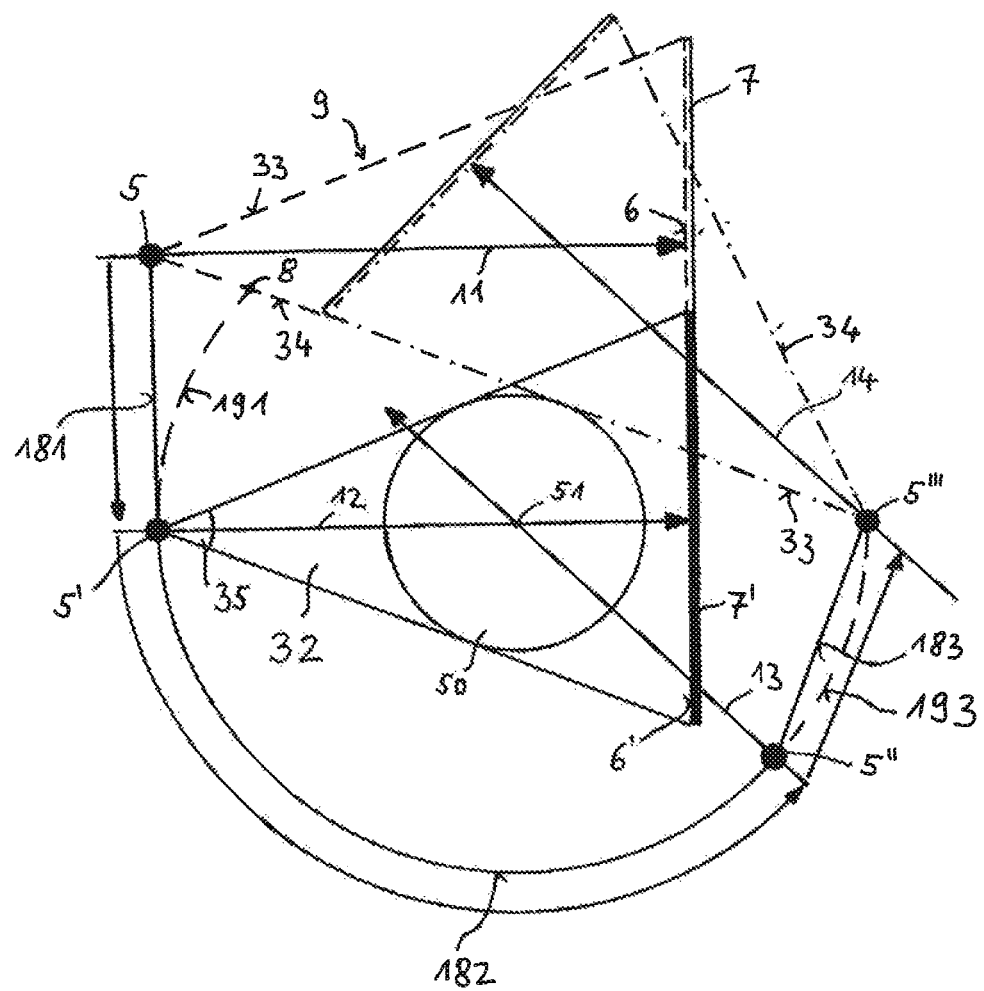
FIG. 2 illustrates focus trajectory and projection geometries for recording a complete projection data set.

FIG. 2 shows two focus trajectories of the focus 5, 5',5", 5'" and of the associated central beam vectors 11, 12, 13, 14 for the sake of example, with which a complete projection data set for the ROI 50 in the plane of the C-arm 2 can be achieved.

FIG. 2 shows an X-ray image recording system 9 having a focus 5, an x-ray beam detector designed as a flat-panel detector (FPD) 7, and a central beam vector 11 which extends from the focus 5 to the center 6 of the beam entry window 6. The focus 5, 5', 5", 5'" is moved along a focus trajectory that consists of three portions 181, 182, 183, wherein the central beam vector 11, 12, 13, 14 is moved in parallel in a stationary coordinate system in the first portion 181 of the first focus trajectory and in the third portion 183 of the first focus trajectory. The second portion 182 of the first focus trajectory is characterized by a rotation of the central beam vector 12, 13 about the virtual scan center 51 in the center of the ROI 50, wherein the curve shape of embodiments of the invention is not a circle but rather a parameterized piece-wise defined superellipse. In FIG. 2, the ROI 50 in the plane of the C-arm 2 and the cone beam extending between the focus 5' and the FPD 7' are shown only in the cone beam 32 situated in this plane with the first and second limiting beams 34, 33. The first limiting beam 34 of the cone beam 32 is on the side of the central beam vector (11, 12, 13, 14) facing away from the C-arm (2), and the second limiting beam 33 of the cone beam 32 is on the side of the central beam vector (11, 12, 13, 14) facing the C-arm (2). All the cone beams with which the projection recordings are recorded during the traversing of the first focus trajectory are situated in the plane of the C-arm 2, and the entire region of the disc-shaped ROI 50 in the central layer having a circular cross-sectional surface is completely contained in the cone beam in each of the one-dimensional projections. The ROI of the example comprises an arrangement of voxels that represent a disk having the height of one voxel.

First the focus 5' at the beginning of the second portion 182 of the first focus trajectory will be considered. The cone beam 32 with a cone angle 35 penetrates the ROI 50 completely. The rotational angle between the positions of the focus 5' and 5" in the second portion 182 of the first focus trajectory is 180° minus the cone angle 35. The distance of the focus 5' from the virtual scan center 51 can be varied along the orbital angle of rotation without detriment to the subsequent 3D reconstruction, so long as the ROI 50 is contained completely in the cone beam of the central layer.

If two portions 191 and 193 of a second focus trajectory were adjoined to the second portion 182 of the focus trajectory, wherein the central beam vector would pass through the virtual scan center 51, then the situation of a cone beam scan with a rotation angle range of 180° plus the cone angle 35 would exist. This represents the known condition for obtaining a complete projection data set for the reconstruction of the ROI 50 in the plane of the C-arm 2 if the focus of the endpoint 8 of the first portion 191 of the second focus trajectory rotates up to the position of the focus 5'" about the virtual scan center 51 with a rotational angle range of 180° plus the cone angle. If one considers a focus at the endpoint 8 with a central beam through the virtual scan center 51, then the cone beam is delimited by the second limiting beam 33, wherein the cone beam in the position of the focus 5'" is delimited for a central beam through the virtual scan center 51 by the first limiting beam 34, which coincides with the second limiting beam 33.

In the method according to certain embodiments of the invention for recording a complete projection data set for the reconstruction of the ROI 50 in the plane of the C-arm 2, the second portion 182 of the first focus trajectory is adjoined by a first portion 181 and a third portion 183 of the first focus trajectory, in which portions the central beam vector 11, 12, 13, 14 is displaced in parallel. The first limiting beam 34 coincides in the position of the focus 5 at the beginning of the first portion 181 of the first focus trajectory with the second limiting beam 33 in the position of the focus 5'".

The parallel movement of the central beam vector with a movement of the focus 5 up to a position of the focus 5' in the first portion 181 of the first focus trajectory and a movement of the focus 5" up to a position of the focus 5'" in the third portion 183 of the first focus trajectory supplements the incomplete projection data set that was obtained in the second portion 182 of the first focus trajectory for a rotation of the central beam vector 12, 13 by an angle of 180° minus the cone angle 35 to form a complete projection data set. Every point within the ROI 50 is crossed by projection beams at angles between 0° and 180° with respect to a coordinate axis connected to the ROI through the virtual scan center.

During the parallel movement of the central beam vector 11, 12, 13, 14, the ROI 50 is irradiated in the first portion 181 of the first focus trajectory with an increasingly larger part of the cone beam 32, whereas the ROI 50 is irradiated with an increasingly smaller part of the cone beam 32 in the parallel movement of the central beam 11, 12, 13, 14 in the third portion 183 of the first focus trajectory. The parts of the cone beam 32 that do not strike the ROI 50 are excluded by using a movable and automatically controlled primary beam diaphragm between the x-ray source and the ROI. The primary beam diaphragm, preferably controlled by an electric motor, is preferably moved synchronously with the movement of the holder 23.

The paths on which the focus 5, 5', 5", 5'" is moved in the first and the third portions of the focus trajectory can be selected largely at will as long as the ROI 50 or a patient table, not shown, do not collide with the x-ray beam source 3, the x-ray beam receiver 4 or the C-arm 2 in FIGS. 1A-1D. In particular, the direction in which the focus trajectory is traversed is irrelevant. Traversing the focus trajectory in one direction or in the other direction supplies identical projection data sets.

It is evident from FIG. 2 that, in the first portion 181 of the first focus trajectory during the movement of the focus 5 in the direction of the position of the focus 5', the distance of the focus 5, 5' from the virtual scan center 51 is greater than the distance of the focus 5', 5" in the region of the second portion 182 of the first focus trajectory having the rotational movement, and that in the third portion 183 of the first focus trajectory during the movement of the focus 5" in the direction toward the position of the focus 5''', the distance of the focus 5', 5''' from the virtual scan center 51 is smaller than the distance of the focus 5', 5" in the region of the second portion 182 having the rotational movement of the central beam vector. The second portion 182 of the first focus trajectory can be adjoined, for example, by the first and third portions 191, 193 of the second focus trajectory, wherein the focus 5, 5', 5", 5''' would be moved on a circular path having a rotational angle of 180° plus the cone angle, and the central beam vector 11, 12, 13, 14 in the first and third portions 191, 193 of the second focus trajectory would be displaced with an unchanged direction in parallel.

FIG. 3 represents the controller architecture for a cone-beam C-arm X-ray apparatus 1 that is suitable for performing the method according to embodiments of the invention for recording a complete projection data set. A movement controller 41 controls all the motorized movements of the cone-beam C-arm X-ray apparatus 1. In the example of FIGS. 1A-1D, the horizontal movement axis 26, the vertical movement axis 27 and the orbital movement axis 25 are provided as motorized axes. By means of the horizontal movement axis 26, the vertical movement axis 27 and the orbital movement axis 25 with a C-arm 2 that is vertical in the room, it is possible to simulate an isocentric C-arm in the movement phase of the rotational scan and to displace the holder 23 of the C-arm 2 in parallel in this plane. By means of the movement controller 41, the movement of the preferably electric motor-controlled primary beam diaphragm can be controlled synchronously with the movement of the holder 23 in such a manner that the part of the cone beam 32 that lies outside the ROI 50 is excluded in the first portion 181, 191 of the focus trajectory and in the third portion 183, 193 of the focus trajectory.

It is within the scope of certain embodiments of the invention to implement the method for recording a projection data set with planar focus and detector trajectories by using a cone-beam C-arm X-ray apparatus 1 in which the C-arm plane is pivoted in space against the vertical. For this purpose, an additional motorized movement axis is provided, which enables a motor-controlled movement transversely to the horizontal movement axis 26 and the vertical movement axis 27. This additional movement axis can be a transverse movement axis in which the holder 23 of the C-arm 2 can be displaced perpendicular to the plane defined by the directions of the horizontal movement axis 26 and the vertical movement axis 27.

A collision protection function can be integrated into the movement controller. It can be provided that alternative focus trajectories for the X-ray focus differing from the planned focus trajectory can be automatically traversed by the movement controller 41 if there is a threat of a collision between parts of the cone-beam C-arm X-ray apparatus 1 and parts of the patient table. All the processes that are connected with the X-ray image generation and X-ray image recording during the scan can be controlled by an image-recording controller 42. The two controllers 41, 42 are synchronized by the central computing unit 40, which has input means 43 and output means 44. Means for the image processing and for the 3-D reconstruction from the recorded projection data are integrated into the central computing unit.

Figure 4:
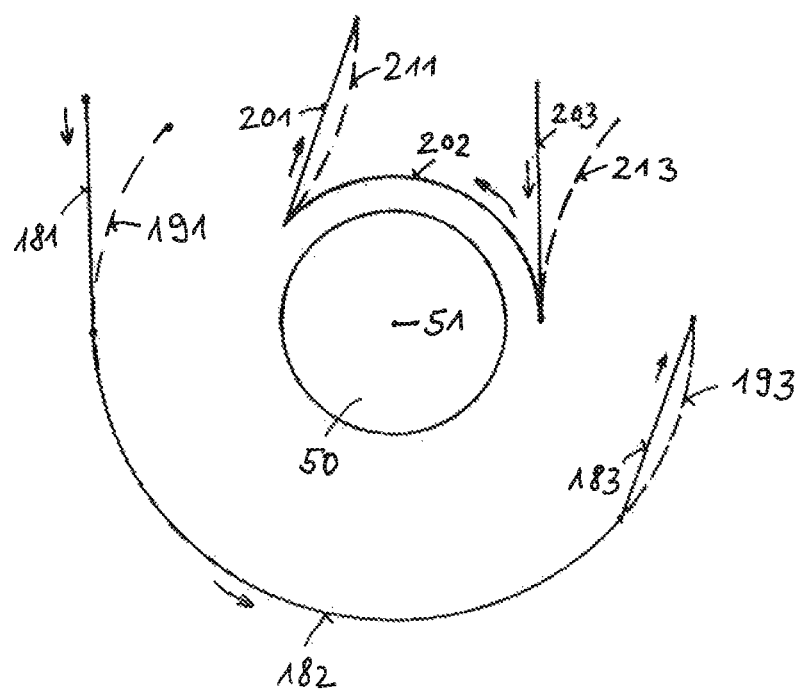
FIG. 4 illustrates second focus trajectory and second detector trajectory for recording a complete projection data set, with circular-arc-shaped rotational trajectories.

FIG. 4 presents a focus trajectory and a detector trajectory of the center point of the beam entry window in the X-ray beam detector for the method for recording a complete projection data set known from German Patent DE102013013552B3 of the applicant, which is hereby incorporated by reference in its entirety.

The first focus trajectory of the focus 5, comprising the portions 181, 182, 183, is traversed in the direction of the arrow. The associated first detector trajectory has the portions 203, 202, 201, which are traversed one after another. If the focus 5 is traversed along a focus trajectory that comprises the first portion 191 of the second focus trajectory, the second portion 182 of the first focus trajectory and the third portion 193 of the second focus trajectory, then the center point of the beam entry window 6 and thus the tip of the central beam vector 11, 12, 13, 14 initially moves on the first portion 213 of the second detector trajectory, then on the second portion 202 of the first detector trajectory and finally on the third portion 211 of the second detector trajectory.

The method for recording a scan of a measurement field ROI (50) having a virtual scan center (51) in the center of the ROI (50) has a scan that consists of a series of X-ray projection recordings that provide a complete set of X-ray projection data of the ROI (50) in the central layer in the plane of the C-arm (2) for a 3D reconstruction. The series of X-ray projection recordings is recorded by using a cone-beam C-arm X-ray apparatus (1) which has a C-arm (2) with a spatially fixed plane, in which the C-arm (2) can be displaced in parallel with a multiply motor-adjustable holder (23) and is supported in the holder (23) movably along the periphery of the arm in an orbital movement axis (25) between a first and a second extreme position, and wherein the C-arm (2) has an X-ray image recording system (9) having an X-ray beam source (3) arranged at one end of the C-arm (2) and an X-ray beam detector (4) arranged oppositely at the other end of the C-arm (2), wherein the holder (23) engages in the first extreme position at one end of the C-arm (2) with the X-ray beam source (3) and wherein the holder (23) engages in the second extreme position at the other end of the C-arm (2) with the X-ray beam detector (4) and wherein the X-ray image recording system (9) is characterized by a central beam vector (11, 12, 13, 14) perpendicular to the beam entry window (6) of the X-ray beam detector (4) and extending from the focus (5, 5', 5", 5''') of the x-ray beam source (3) to the center of the beam entry window (6) of the X-ray beam detector (4) and generates a cone beam that contains a cone beam (32) having a cone angle (35) in the plane of the C-arm (2), wherein the focus (5, 5,', 5", 5''') of the X-ray beam source (3) is moved along a planar contiguous focus trajectory between a starting point and an ending point in an arbitrary direction to record the series of X-ray projection images.

At the starting point of the focus trajectory, the C-arm (2) is positioned in the first extreme position and in the orbital movement axis (25) the movable holder (23) of the C-arm (2) is positioned such that a first limiting beam (34) of the cone beam (32) on a side of the central beam vector (11, 12, 13, 14) facing away from the C-arm (2) is tangent with the ROI (50).

In a first portion (181, 191) of the focus trajectory, the holder (23) is displaced in parallel in the plane of the C-arm (2) until the central beam vector (11, 12, 13, 14) runs through the virtual scan center (51) and the ROI (50) is completely inside the cone beam (32).

In a second portion (182) of the focus trajectory, the C-arm (2) is moved in the orbital movement axis (25) from the first extreme position into a second extreme position, in which the holder (23) engages at the other end of the C-arm (2) with the X-ray beam detector (4), wherein the angle range of the orbital movement between the first and the second extreme positions is at least 180° minus the cone angle (35), and the holder (23) is displaced in parallel in the plane of the C-arm (2) in such a manner that the central beam vector (11, 12, 13, 14) runs through the virtual scan center (51) and the ROI (50) is completely inside the cone beam (32), and the trajectory of a point in the center of the input window of the FPD has the shape of a circular arc.

In a third portion (183, 193) of the trajectory, which transitions continuously from the trajectory of the second portion, the C-arm (2) remains in the second extreme position in the orbital movement axis (25) and the holder (23) is displaced in parallel in the plane of the C-arm (2) until a second limiting beam (33) of the cone beam (32) on the side of the central beam vector (11, 12, 13, 14) facing the C-arm (2) is tangent with the ROI (50).

In addition to the rotational detector trajectory 202 in the form of a circular arc as illustrated in FIG. 4, there are also rotational detector trajectories for mobile X-ray diagnostic devices in which the central beam always runs in the form of ellipses through the virtual scan center, wherein both the circular arc-shaped and the elliptical rotational detector trajectories are stored as curve bundles in a lookup table (LUT) of the movement controller 41 of the central computing unit 40 or are calculated in real time in the central computing unit and transmitted to the movement controller.

It is provided that a pair of trajectories can be selected from the curve bundles of trajectories that are stored in the movement controller of the X-ray apparatus and retrieved if necessary and traversed in a scan.

Precisely for heavy set patients or virtual scan centers which are positioned off-center relative to the patient longitudinal axis, trajectories with circular arc shaped or elliptical rotational trajectories often lead to collisions of the detector or the X-ray source with the patient body or with parts of the patient table, so that a prescribed range of orbital angles cannot be completely traversed in a scan. It is known that if the circular radius or the semi-axis of an ellipse is enlarged, the movement range of the linear displacement axes of the C-arm holder is no longer sufficient to be able to completely traverse translational trajectory portions adjoining the rotational part of the trajectory with an increased collision-free volume in order to achieve a complete angle coverage in the central layer.

The respective trajectories can be stored by triplets of values of the adjustment axes (horizontal, vertical, orbital) or by functions with stored parameters. In both cases, the linear displacement axes and the orbital axis of the C-arm are moved in a scan along the value triplets retrieved from the memory or along the value triplets calculated from a stored function.

In the bundle of stored trajectories, a trajectory assumed to be suitable for a prescribed imaging task is selected before the performance of a scan. The selection is manual or preferably automatic. In an automatic selection of a suitable trajectory, it is preferred to utilize the selection made in an organ program for the imaging task.

The organ program contains information on the position of the virtual scan center inside the patient's body. A selection possibility for the patient thickness is also advantageously provided in the organ program.

Information on the thickness and/or the cross-section of the patient and/or the patient table can also be obtained by prior measurements of the patient and/or the patient table surface by scanning with distance sensors or by optical means.

The manual determination of a patient envelope curve from a bundle of patient envelope curves stored in the movement controller is also provided.

To perform a predetermined imaging task, a scan is carried out with the selected detector trajectory and the associated focus trajectory or equivalently with a selected focus trajectory and the associated detector trajectory from the memory of the movement controller. Preferably a scan without X-ray radiation is initially simulated for the purpose of checking the collision-freeness of the trajectories. If a collision danger is detected in a simulated scan, a different trajectory, which will assure collision-freeness at the point of the detected collision danger, is selected from the memory.

In the event of a detected collision danger during a simulated scan, it is provided that the C-arm can be adjusted manually by an operator in such a manner that the detector or the radiation emitter housing is moved away from the patient or the patient table. Taking into account the manual adjustment paths present in the movement controller after the manual adjustment, an alternative and presumably collision-free trajectory is preferably automatically selected and used for another simulated scan.

If a simulated scan with a selected pair of detector and focus trajectories of the C-arm has passed through the predetermined path curve completely without collisions, then a scan with X-ray radiation is carried out with the same trajectory pair and the recorded X-ray projections are stored for a subsequent 3D reconstruction.

The trajectories with which a larger collision-free volume or/and a better adjustment of the scan trajectories to the patient dimensions and the imaging task can be achieved are generated by establishing a relationship in the rotational part with piece-wise functions such as manifolds
superellipses
Bezier curves
polynomials
or other mathematical functions that relate the positions of a reference point (e.g. in the center of the input window of the detector) to the orbital rotation angle.

Superellipses, in which the rotational position of the superellipse is variable, have been recognized as suitable functions for advantageously solving the problem.

A superellipse with semi-axes a and b along the coordinate axes is defined mathematically by Formula 1 as follows:

$$\left|\frac{x}{a}\right|^m + \left|\frac{y}{b}\right|^n = 1$$

In the formula, m and n are parameters that determine the shape of the superellipse. It is possible to set m=n without significantly losing flexibility. If, without loss of generality, the center point of the superellipse is placed at the coordinate origin, then the following Formula 2 results for the representation of a superellipse in polar coordinates:

$$r(\theta) = \frac{ab}{\sqrt[n]{|a\sin(\theta-\theta_0)|^n + |b\cos(\theta-\theta_0)|^n}}$$

In Formula 2, r represents the distance of the virtual isocenter/virtual scan center from a reference point (for example in the center of the entry window of the FPD), a and b determine the two semi-axes, θ represents the polar coordinates (e.g. defined by the angle of the orbital displacement) and θ0 represents an angle that determines the rotational position of the superellipse about the origin.

In the case where n=2, regular ellipses are obtained; if one further sets a=b, then a circle is obtained as a special case of a superellipse. The parameter n is referred to as a shape parameter. Superellipses with a shape parameter n≠2 are then used to move the reference point toward or away from the patient.

The shape parameter n can depend on the angle θ of the orbital displacement. With a shape parameter n(θ) dependent on the angle θ of the orbital displacement, a trajectory composed of piecewise defined superellipses can be produced. The use of continuous and non-continuous shape parameters n(θ) for the rotational portions of the trajectories is provided. A non-continuous shape parameter n(θ) leads to trajectories in which, at a defined angle θ of the orbital displacement, there is a discontinuity with a reduction or increase of the distance of the reference point on the detector from the virtual scan center. Non-continuous trajectories are also provided in which the trajectory is formed piecewise by different superellipses before and after the discontinuity. In addition, trajectories are provided which are continuous and have a continuously varying shape parameter n(θ) or also semi-axes a(θ) and b(θ) dependent on the angle θ and the rotational position angle θ0(θ).

To define the trajectories, the angle intervals for the orbital angles θ are stored in the memory of the movement controller together with a set of parameters defining superellipses or with a set of functions n(θ), a(θ), b(θ) and θ0(θ). If the C-arm is moved according to a selected rotational trajectory, then the reference point of the x-ray detector for example passes through the respective superellipses stored as a parameter set in the defined intervals of the orbital angle displacement, or continuously changes the parameters n, a, b and θ0 according to the stored functions. In this case the rotational trajectories are stored in the form of manifolds, which only correspond to a superellipse in a local infinitesimal rotational portion.

The use of piecewise defined superellipses as a function of the angle θ of the orbital displacement as a focus or detector trajectory makes it possible that, for a large number of combinations of the imaging task defined by the organ program, the patient thickness and the dimensions of the patient table, collision-free rotational portions of trajectories can be generated, with which a complete projection data set in the central layer can be generated when the trajectories are supplemented with translational components.

Figure 5:
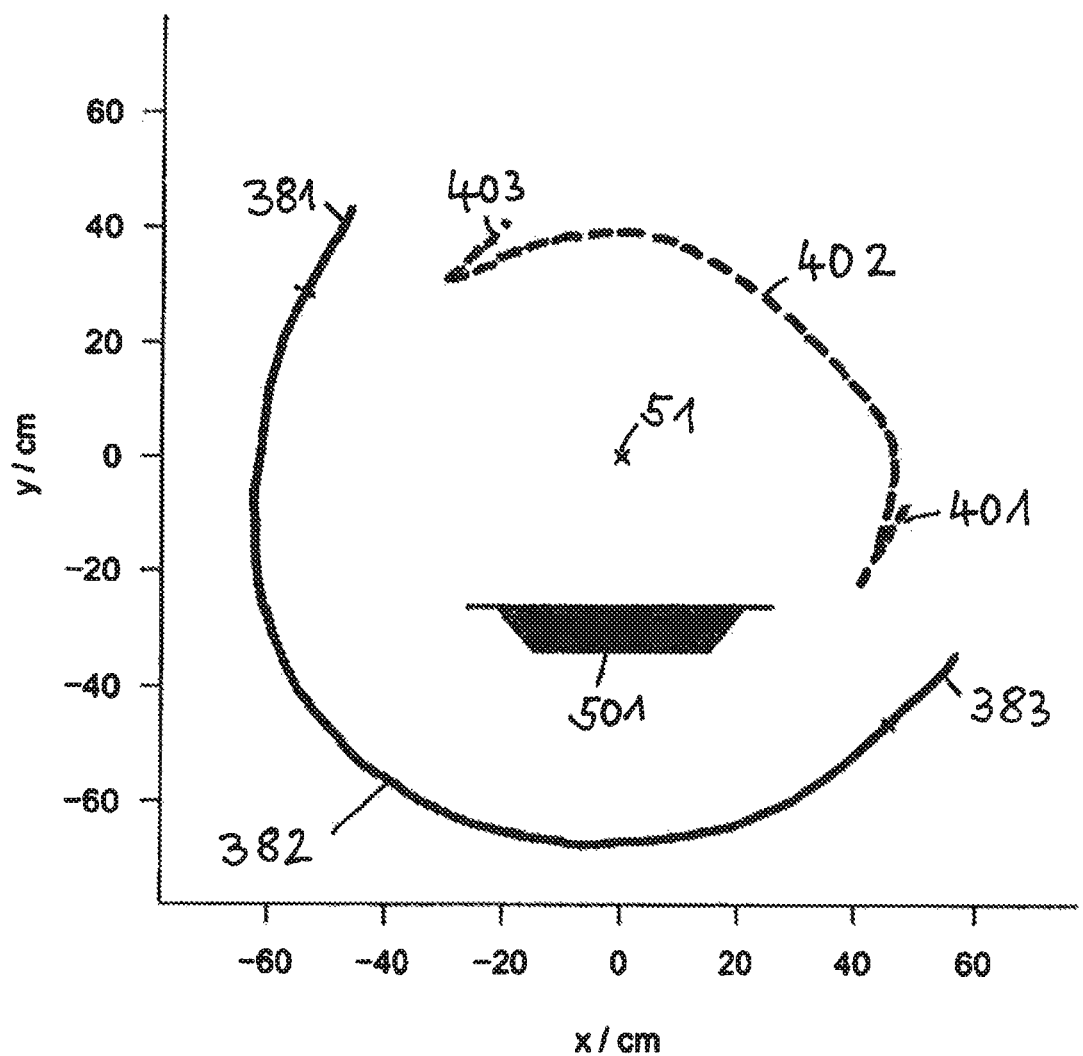
FIG. 5 illustrates focus trajectory and detector trajectory for a centrally located virtual scan center, with a rotational portion of the detector trajectory that is formed from superellipses.

FIG. 5 shows a view of the focus trajectory (381, 382, 383) and the detector trajectory (401, 402, 403) for a centrally positioned virtual scan center (51) with a portion of the detector trajectory (402) formed from superellipses in the scan plane. The patient longitudinal axis and the longitudinal axis of the tabletop (501) of the patient table are selected in the representation such that they are perpendicular to the scan plane. The virtual scan center (51) lies above the central axis of the tabletop (501) of the patient table. In an organ program, this corresponds to the imaging task for a spinal operation, for example. The representation has scales of the horizontal adjustment axis of the C-arm holder in the x-direction and the vertical adjustment axis of the C-arm holder in the y-direction. The virtual scan center (51) has the coordinates x=0, y=0.

Figure 6:
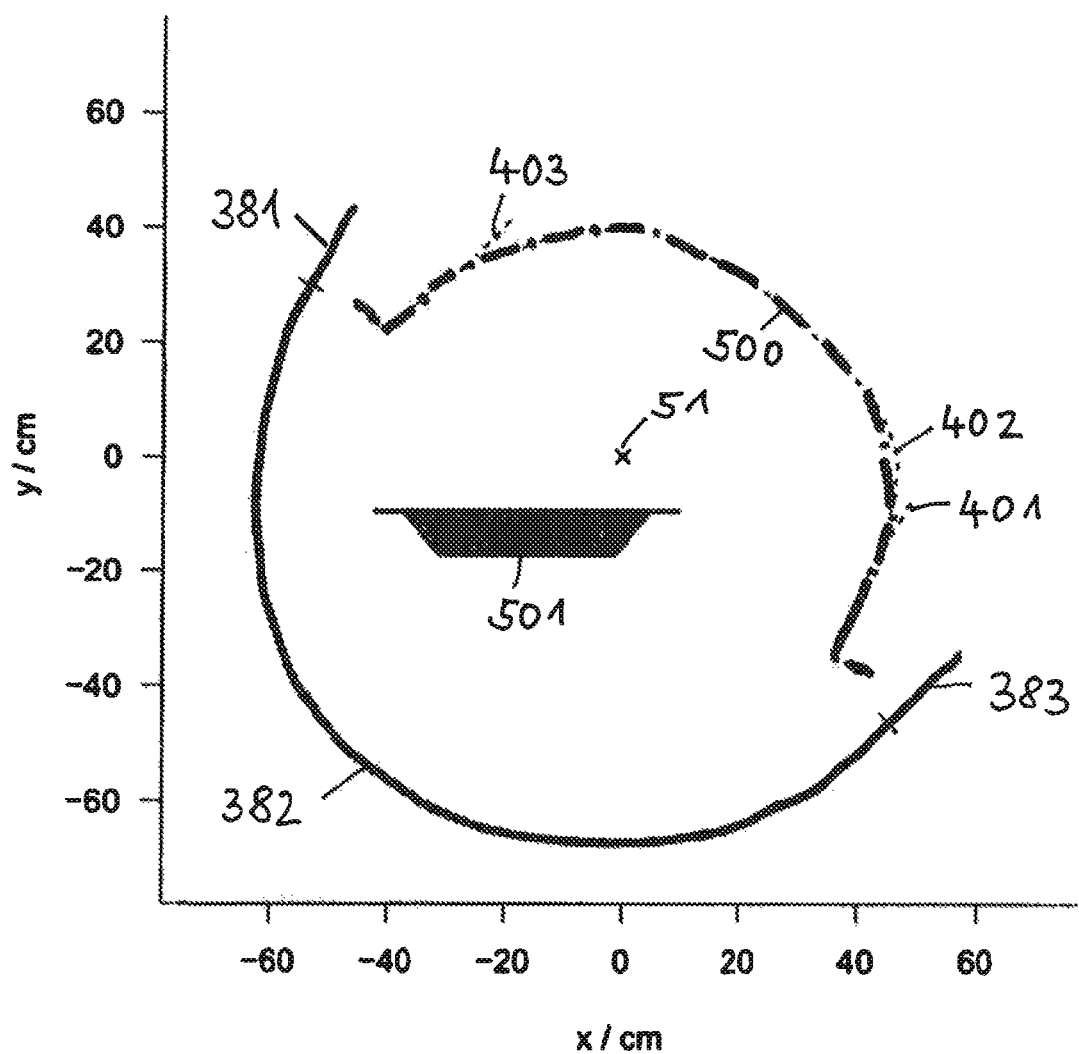
FIG. 6 illustrates focus trajectory and detector trajectory for an eccentrically located virtual scan center, with a rotational portion of the detector trajectory that is formed from superellipses.

FIG. 6 shows a view of the focus trajectory (381, 382, 383) and the detector trajectory (401, 402, 403) for an eccentric virtual scan center (51) with a portion of a detector trajectory (402) formed from superellipses in the scan plane. The patient longitudinal axis and the longitudinal axis of the tabletop of the patient table (501) are selected in the representation so as to be perpendicular to the scan plane, as in FIG. 5. The virtual scan center (51) is laterally offset above the central axis of the tabletop (501) of the patient table. In an organ program, this corresponds to the imaging task in an examination of the shoulder joint, for example. As a part of the focus trajectory, the detector-side limiting line (500) of the collision-free cross-sectional area in the scan plane is drawn in the diagram. The limiting line (500) was determined for an FPD with a surface of 30×30 cm. This limiting line is obtained by determining, for every scan position, the cross-section of the FPD associated with a central beam position in the scan plane. It can be seen that a collision-free scan is possible for the shoulder position that is shown, but that a different detector trajectory would have to be selected for the opposite shoulder in order to avoid collisions during the scan.

The focus trajectory (381, 382, 383) and the detector trajectory (401, 402, 403) are identical in FIGS. 5 and 6. The virtual scan center (51) is defined to be spatially fixed in the coordinate system of the cone-beam C-arm X-ray apparatus. The point of interest (POI) inside an ROI in the patient is selected based on the given imaging task by an operator from an organ program stored in the memory of the x-ray apparatus. To perform a scan around the virtual scan center (51), the point of interest POI must first be made to coincide with the virtual scan center. For this purpose, the horizontal and the vertical adjustment axes of the C-arm holder are brought into a predetermined base position and in this base position, the chassis of the cone-beam C-arm x-ray apparatus is moved on the floor in such a manner that a vertical central beam runs through the ROI. The adjustment can be done in part by adjusting the horizontal adjustment axis of the C-arm holder. The horizontally adjusted central beam is aligned with the POI by adjusting the height of the patient table or by adjusting the vertical adjustment axis of the C-arm holder.

The alignment of the POI with the virtual scanning center (51) is only allowed by the movement controller of the cone beam x-ray apparatus if sufficiently long adjustment paths in the X and Y directions for traversing the trajectories are available. Otherwise the undesired case can occur that a rotational portion or translational portions of the trajectories cannot be completely traversed, which leads to an incomplete 3D data set. The user of the X-ray system is provided by the controller of the cone-beam C-arm X-ray apparatus with a scanning alternative that has an angle coverage of less than 180° if the conditions for the POI and the patient, as well as the table cross-section, do not permit the recording of a complete 3D data set. The user is prompted to consent to the recording of an incomplete 3D data set by making an input into the central unit.

The selected detector trajectory and the associated focus trajectory are traversed by motor-driven movement of the C-arm in the horizontal x-axis, the vertical y-axis and the orbital axis and x-ray projections are automatically recorded at points of the trajectories that are predetermined or dynamically determined during the scan. The positions at which an X-ray projection is to be recorded on a selected trajectory depend on the size of the FPD in the direction of the orbital adjustment axis and on the distance of the reference point from the virtual scan center. The positions or a rule for calculating the positions for recording X-ray projections are stored together with the trajectories in the memory of the movement controller.

The selected detector trajectory and the associated focus trajectory are converted in the movement controller (41), by means of the known inverse kinematics of the cone-beam C-arm X-ray apparatus during the scan, into the values of the horizontal x-axis, the vertical y-axis and the orbital axis that are to be adjusted.

The disclosure herein provides a method for generating a sequence of 2D x-ray projections for a 3D data set, complete in the central axis for a volume reconstruction, by using an X-ray system having a cone-beam C-arm X-ray apparatus (1) comprising a holder (23), displaceable in at least two spatial directions, for an X-ray image recording system (9) having a C-arm (2), which can be displaced in the holder (23) along the periphery of the arm, the C-arm (2) having an X-ray source (3) with a focus (5) and a flat panel detector (FPD 7) as an X-ray beam detector (4) with a reference point in the center of the beam entry window (6) of the X-ray beam detector (4), comprising the steps:

a) receiving an input for determining an organ program for performing an imaging task, by which organ program a POI in a section plane of a patient body and an envelope curve of the patient cross-section and the cross-section of the tabletop of the section plane in the coordinates of a coordinate system connected to the tabletop of the patient table are defined. In the selection of the organ program it is provided to take account of the thickness of the patient and optionally to input the cross-section of the envelope curve of the patient and of the tabletop (501) of the patient table into the central computing unit (40) of the cone-beam C-arm X-ray apparatus (1) by means of a graphical user interface GUI in the input means (43). The envelope surface can be determined with optical or electromagnetic measuring transducers or by two X-ray projections of different projection geometry and can be input into the X-ray system. It is also provided to determine the position of the POI by evaluating two X-ray projections of different projection geometry.

b) receiving an input for selecting a pair composed of a detector trajectory (401, 402, 403) and an associated focus trajectory (381, 382, 383), each having a rotational portion, from the provision of a plurality of stored trajectory pairs represented by parameters in a memory of the central computing unit (40), wherein the rotational part of the detector trajectory (402) and the rotational part of the focus trajectory (382) deterministically follow from the trajectory of a reference point rigidly connected thereto located on the X-ray imaging system (9) and which is formed piecewise from superellipses with the formula $$r(\theta) = \frac{ab}{\sqrt[n]{|a \sin(\theta - \theta_0)|^n + |b \cos(\theta - \theta_0)|^n}}$$

in polar coordinates, where $r(\theta)$ represents the distance of the virtual scan center (51) from the reference point, which distance depends on the angle $\theta$ of the orbital adjustment of the C-arm, a and b determine the two semi-axes of the superellipse, $\theta 0$ represents an angle that indicates the rotational position of the superellipse about the origin and n represents a shape parameter, wherein the envelope curve of the patient cross-section and of the tabletop are arranged collision-free within the cross-section of the volume defined by the FPD housing and the x-ray emitter housing during a virtual scan. It is provided that the superellipses have semi-axes $a(\theta)$ and $b(\theta)$ dependent on the angle $\theta$ of the orbital adjustment, a shape parameter $n(\theta)$ and a rotational position angle $\theta 0(\theta)$. It is further provided that the semi-axes $a(\theta)$ and $b(\theta)$, the shape parameter $n(\theta)$ and the rotational position angle $\theta 0(\theta)$ or the mathematical derivatives thereof are not continuous in relation to the angle $\theta$ of the orbital displacement. It can optionally be provided before this step that an input is received by which there is a selection between two possibilities, wherein if the first possibility is chosen, the detector trajectory (402) is determined such that the FPD (7) is guided collision-free relative to the envelope curve as closely as possible to the virtual scan center (51) and if the second possibility is chosen, the detector trajectory (402) is determined such that the FPD (7) is guided collision-free relative to the envelope curve as far removed as possible from the virtual scan center (51).

c) outputting the detector trajectory and the focus trajectory of the selected trajectory pair to the movement controller (41) in the coordinates of the horizontal x adjustment axis and the vertical y adjustment axis and outputting the x and y coordinates of a base position of the C-arm holder (23), in which the central beam of the C-arm runs through the virtual scan center for all orbital angle positions and adjusting the base position of the holder (23) of the C-arm (2) by motor-powered displacement in the horizontal and the vertical adjustment axes.

d) outputting the position of the POI and the patient section plane with respect to a coordinate system connected to the floor (22).

e) aligning the cone-beam C-arm X-ray apparatus (1) in the base position by displacing the chassis of the cone-beam C-arm X-ray apparatus (1) along the floor (22) relative to the tabletop (501) in such a manner that both the plane of the C-arm and the virtual scan center (51) coincide with the patient section plane and the POI with the virtual scan center (51) in the patient.

f) traversing the trajectory pair selected in step b) by motor-powered movement of the C-arm (2) in the horizontal x-axis, the vertical y-axis and the orbital axis and automatically recording x-ray projections at positions that are predetermined and stored together with the trajectories, or are determined dynamically during the scan.

It is provided that the trajectory pair is selected by means of an algorithm in which the POI in the interior of the patient is made to coincide with the virtual scan centers (51) of the stored trajectory pairs, and the envelope curve of the patient cross-section and of the tabletop is compared to the cross-sections of the volume defined by the FPD housing and by the X-ray emitter housing during the virtual scan until collision-freeness between the envelope curve and the C-arm (2) has been determined.

It is further provided that a trajectory pair in the memory of the movement controller (41) is assigned to each selected organ program.

To perform the method steps, an X-ray system having a cone-beam C-arm X-ray apparatus (1) is provided, comprising a holder (23) displaceable in at least two spatial directions by linear adjustment elements for a C-arm (2) that has an X-ray recording unit and is orbitally adjustable in the holder (23) along the periphery of the arm, wherein the X-ray recording unit supports an X-ray beam source (3) and an X-ray beam detector (4), the system comprising a chassis with which the cone-beam C-arm X-ray apparatus (1) can be moved along the floor (22), and comprising a central computing unit (40) that is designed:

a) to receive a first input and, based on this first input, to determine an organ program having a POI and a section plane through the patient, an envelope curve of the patient cross-section and the table top (501) in the coordinates defined relative to the patient, b) to receive a second input and, based on this second input, to select and determine for the determined envelope curve and the POI a pair composed of a detector trajectory (402) and an associated focus trajectory (382) from the provision of a plurality of trajectory pairs stored in the memory of the movement controller (41), c) to receive a third input and, based on this third input, to determine and output the position of the POI and of the patient section plane relative to a coordinate system connected to the floor (22), d) to control the linear adjustment elements and the orbital adjustment elements for the C-arm (2) in such a manner that the determined trajectory pair is traversed by motor-controlled movement of the C-arm (2) in order to record an x-ray projection in succession at each of the determined positions.

In some embodiments, it is provided that, in addition to the cone-beam C-arm X-ray apparatus, the X-ray system can comprise a patient table having a motor-adjustable tabletop (501), wherein the central computing unit (40) of the cone-beam C-arm x-ray apparatus (1) correlates the adjustment of the tabletop of the patient table with the movement of the cone-beam C-arm X-ray apparatus (1) and/or takes the position and orientation of the patient table into account in the selection of the trajectory used.

In some embodiments, it is provided that the X-ray system enables a fourth input by which it is determined whether the X-ray projections are to be recorded for achieving a high reconstruction resolution or the largest possible reconstruction volume, wherein the central computing unit (40) determines the trajectory pair in such a manner that the detector trajectory (402) is as far away as possible from the virtual scan center (51) for a high resolution, and the detector trajectory (402) is as close as possible to the virtual scan center (51) for a large reconstruction volume.

Although the foregoing description of the preferred embodiments of the present invention has shown, described and pointed out the fundamental novel features of the invention, it will be understood that various omissions, substitutions, and changes in the form of the detail of the invention as illustrated as well as the uses thereof, may be made by those skilled in the art, without departing from the spirit of the invention. Particularly, it will be appreciated that the preferred embodiments of the invention may manifest itself in other shapes and configurations as appropriate for the end use of the article made thereby.

What is claimed is:

1. A method for generating a sequence of 2D X-ray projections for a 3D data set, complete in the central axis for a volume reconstruction, by using a cone-beam C-arm X-ray apparatus comprising a movement controller and a holder, displaceable in at least two spatial directions by linear adjustment elements having a limited adjustment path, for an X-ray image recording system having a C-arm, which can be displaced in the holder along the periphery of the arm and having a limited orbital adjustment range of less than 180 degrees, the C-arm having an x-ray source with a focus and a flat panel detector as an X-ray beam detector with a reference point in the center of the beam entry window of the x-ray beam detector comprising the steps:

a) a) receiving an input for determining an organ program for performing an imaging task, by which organ program a point of interest (POI) in a section plane of a patient body and an envelope curve of the patient cross-section and the cross-section of the tabletop of the section plane in the coordinates of a coordinate system connected to the tabletop of the patient table are defined, b) receiving an input for selecting a pair comprising a detector trajectory and an associated focus trajectory, each having a rotational portion and comprising two interconnected repeater sections at each end of the rotational parts, from the provision of a plurality of stored trajectory pairs represented by parameters in a memory of the central computing unit, wherein the rotational part of the detector trajectory and the rotational part of the focus trajectory deterministically follow from the trajectory of the reference point rigidly connected thereto located on the X-ray imaging system and which is formed piecewise from superellipses with the formula $$r(\theta) = \frac{ab}{\sqrt[n]{|a\sin(\theta-\theta_0)|^n + |b\cos(\theta-\theta_0)|^n}}$$

in polar coordinates, where $r(\theta)$ represents the distance of the virtual scan center from the reference point, which distance depends on the angle $\theta$ of the orbital adjustment of the C-arm, a and b determine the two semi-axes of the superellipse, $\theta_0$ represents an angle that determines the rotational position of the superellipse about the origin and n represents a shape parameter, wherein the envelope curve of the patient cross-section and of the tabletop are arranged collision-free within the cross-section of the volume defined by the FPD housing and the x-ray emitter housing during a virtual scan, c) outputting the detector trajectory and the focus trajectory of the selected trajectory pair to the movement controller in the coordinates of the horizontal x-adjustment axis and the vertical y-adjustment axis and outputting the x and y coordinates of a base position of the C-arm holder, in which the central beam of the C-arm runs through the virtual scan center for all orbital angle positions and adjusting the base position of the holder of the C-arm by motor-powered displacement in the horizontal and the vertical adjustment axes, d) outputting the position of the POI and the patient section plane with respect to a coordinate system connected to the floor, e) aligning the cone-beam C-arm X-ray apparatus in the base position by displacing the chassis of the cone-beam C-arm x-ray apparatus along the floor relative to the tabletop in such a manner that both the plane of the C-arm and the virtual scan center coincide with the patient section plane and the POI with the virtual scan center in the patient, and f) traversing the trajectory pair selected in step b) by motor-powered movement of the C-arm in the horizontal x-axis, the vertical y-axis and the orbital axis and automatically recording x-ray projections at positions that are predetermined and stored together with the trajectories, or are determined dynamically during the scan.

2. The method for generating a sequence of 2D X-ray projections according to claim 1, characterized in that the movement controller additionally provides for a collision protection function, which at a time of collision danger between the two parts of the cone-beam C-arm X-ray apparatus and parts of the table top can choose an alternative focus trajectory different from the programed focus trajectory and will autonomously execute via the movement controller.

3. The method for generating a sequence of 2D X-ray projections according to claim 1, characterized in that the trajectory pair is selected by means of an algorithm in which the POI in the interior of the patient is made to coincide with the virtual scan centers of the stored trajectory pairs and the envelope curve of the patient cross-section and of the tabletop is compared to the cross-sections of the volume defined by the FPD housing and by the x-ray emitter housing during a virtual scan until collision-freeness between the envelope curve and the C-arm has been determined.

4. The method for generating a sequence of 2D X-ray projections according to claim 1, characterized in that the a trajectory pair in the memory of the movement controller is assigned to each selected organ program.

5. The method for generating a sequence of 2D X-ray projections according to claim 1, characterized in that an input is received before step b), by which there is a selection between two possibilities, wherein if the first possibility is chosen, the detector trajectory is determined such that the FPD is guided collision-free relative to the envelope curve as closely as possible to the virtual scan center and if the second possibility is chosen, the detector trajectory is determined such that the FPD is guided collision-free relative to the envelope curve as far removed as possible from the virtual scan center.

6. The method for generating a sequence of 2D X-ray projections according to claim 1, characterized in that the superellipses in step b) have semi-axes $a(\theta)$ and $b(\theta)$ dependent on the angle $\theta$ of the orbital adjustment, a shape parameter $n(\theta)$ and a rotational position angle $\theta 0(\theta)$.

7. The method for generating a sequence of 2D X-ray projections according to claim 1, characterized in that the semi-axes $a(\theta)$ and $b(\theta)$, the shape parameter $n(\theta)$ and the rotational position angle $\theta 0(\theta)$ or the mathematical derivatives thereof are not continuous in relation to the angle $\theta$ of the orbital adjustment.

8. The method for generating a sequence of 2D X-ray projections according to claim 1, characterized in that the thickness of the patient is taken into consideration in the selection of the organ program in step a).

9. A computer program product that can be installed directly in a memory of a central computing unit of a cone-beam C-arm x-ray apparatus, having program code sections for performing a method according to claim 8.

10. The method for generating a sequence of 2D X-ray projections according to claim 1, characterized in that an envelope surface of the patient and the table top of the patient table is input into the computing unit of the cone-beam C-arm x-ray apparatus by a graphical user interface GUI in the input.

11. The method for generating a sequence of 2D X-ray projections according to claim 1, characterized in that the envelope surface is determined with optical or electromagnetic measuring transducers prior to step b) and input into the X-ray system.

12. The method for generating a sequence of 2D X-ray projections according to claim 1, characterized in that the POI is determined from two x-ray projections of different projection geometry.

13. An X-ray system suitable for performing the method according to claim 1, having a cone-beam C-arm X-ray apparatus comprising a holder displaceable in at least two spatial directions by linear adjustment elements for a C-arm that has an x-ray recording unit and is orbitally adjustable in the holder along the periphery of the arm, wherein the X-ray recording unit supports an X-ray beam source and an X-ray beam detector, the system comprising a chassis with which the cone-beam C-arm X-ray apparatus can be moved along the floor, and comprising a central computing unit that is configured to:
 a) to receive a first input and, based on this first input, to determine an organ program having a POI and a section plane through the patient, an envelope curve of the patient cross-section and the table top in the coordinates defined relative to the patient,
 b) to receive a second input and, based on this second input, to select and determine for the determined envelope curve and the POI a pair composed of a detector trajectory and an associated focus trajectory from the provision of a plurality of trajectory pairs stored in the memory of the movement controller,
 c) to receive a third input and, based on this third input, to determine and output the position of the POI and of the patient section plane relative to a coordinate system connected to the floor,
 d) to control the linear adjustment elements and the orbital adjustment elements for the C-arm in such a manner that the determined trajectory pair is traversed by motor-controlled movement of the C-arm in order to record an x-ray projection in succession at each of the determined positions.

14. The X-ray system according to claim 13, further comprising a patient table having a motor-adjustable tabletop, wherein the central computing unit of the cone-beam C-arm x-ray apparatus correlates the adjustment of the tabletop of the patient table with the movement of the cone-beam C-arm x-ray apparatus and/or takes the position and orientation of the patient table into account in the selection of the trajectory used.

15. The X-ray system according to claim 13, wherein the system enables a fourth input by which it is determined whether the X-ray projections are to be recorded for achieving a high reconstruction resolution or the largest possible reconstruction volume, wherein the central computing unit determines the trajectory pair in such a manner that the detector trajectory is as far away as possible from the virtual scan center for a high resolution, and the detector trajectory is as close as possible to the virtual scan center for a large reconstruction volume.

* * * * *